United States Patent [19]

Protzman et al.

[11] 4,051,232

[45] Sept. 27, 1977

[54] SEROLOGIC TEST FOR SYSTEMIC CANDIDIASIS

[75] Inventors: Walter P. Protzman, Hopewell; George L. Evans, Hopatcong, both of N.J.

[73] Assignee: Schering Corporation, Kenilworth, N.J.

[21] Appl. No.: 603,896

[22] Filed: Aug. 12, 1975

[51] Int. Cl.² .................... G01N 33/16; G01N 31/02

[52] U.S. Cl. .................... 424/12; 23/230 B; 23/253 TP; 23/259; 195/103.5 A; 195/103.5 M

[58] Field of Search .................... 23/230 B, 259, 292; 195/1.7, 1.8, 99, 100, 103.5 R, 103.5 M, 103.5 A; 424/12

[56] References Cited

U.S. PATENT DOCUMENTS

| | | | |
|---|---|---|---|
| 3,293,145 | 12/1966 | Leavitt et al. | 195/100 X |
| 3,870,600 | 3/1975 | Youssef | 195/103.5 M |
| 3,907,502 | 9/1975 | Brink | 23/230 B |

OTHER PUBLICATIONS

*Chem. Abstr.*, v. 75:33020*h* (1971).

Darcy, *Clin. Chim. Acta*, v. 38, pp. 329–337 (1972).

Evans et al., *Brit. J. Med.*, v. 4 (#5884), pp. 86–87 (1973).

Chem. Abstr., #82:13533*u* (1975).

*Primary Examiner*—Sidney Marantz

*Attorney, Agent, or Firm*—Barbara L. Cowley Renda; Stephen B. Coan; Bruce M. Eisen

[57] ABSTRACT

An in vitro test method for the diagnosis of systemic candidiasis in mammals is carried out with an antigen solution containing a specified concentration and ratio of protein antigen and mannan antigen whereby false readings are reduced.

6 Claims, 1 Drawing Figure

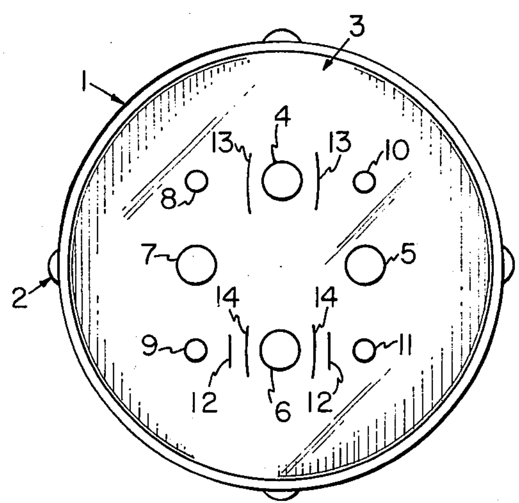
1
2
3
4
5
6
7
8
9
10
11
12
13
14

SEROLOGIC TEST FOR SYSTEMIC CANDIDIASIS

This invention relates to an in vitro test method for the diagnosis of systemic candidiasis. It additionally relates to a test plate and kit for this purpose.

Systemic infections in mammals due to the Candida species of yeast have been recognized since the 1860's. In particular, *Candida albicans* is well-known as an ubiquitous opportunistic yeast that can cause fatal systemic infections in compromised hosts. The increasing use of antibiotics, chemotherapy, open heart surgery, transplants, indwelling catheters, and in general, the prolonging of life of seriously ill people has enabled systemic fungal infections to become much more prevalent.

Should a reliable ddiagnosis of systemic candidiasis be made, then aggressive therapy could be promptly instituted. Since agents against systemic candidiasis, such as amphotericin B, have serious side effects, it is important not to begin such chemotherapy unless clearly warranted.

Unfortunately, systemic candidiasis is difficult to diagnose since the organism *Candida albicans* is readily found on the skin and in the gastrointestinal tract of man. If systemic candidiasis is suspected prior to death, the culturing of *Candida* from body fluids or from biopsy tissue is often attempted. However, the failure rate is high or positive cultures are obtained too late to be of use. Even isolation from blood culture is a problem due to skin contamination or to inhibition of the organism by unknown factors in the blood. Thus, a reliable and rapid detection of antibodies to *C. albicans* in a patient's serum (serologic diagnosis) would be a highly valuable technique.

Many attempts have been made to develop a reliable serologic test for systemic candidiasis. A good summary of such prior art appears in Taschdjian et al. Serological Diagnosis of Candidal Infections, CRC Critical Reviews in Clinical Laboratory Sciences, July, 1973, pgs. 19–59, and references cited therein.

Serodiagnostic approaches include the complement fixation reaction (FCR), direct agglutination, latex agglutination, indirect fluorescent antibody (IFA) reaction and the precipitin reaction. None of these techniques have heretofore (to the best of applicants ' knowledge) produced a reliable test suitable for ordinary clinical laboratory technicians. Convenient tests generally produced too many false negative or false positive readings to be relied upon.

The precipitin reaction approach is based on the prior art observation that certain antibodies are differentially present in the blood serum of a host infected with systemic, as opposed to superficial, candidiasis. These antibodies react with antigens produced by breakdown of the candidal cell contents to form a chemical complex which precipitates. After placing a sample of blood serum in one well of an agar plate (or equivalent gelatinous matrix material), and placing a Candida antigen in a second well, the actives migrate or diffuse through the gel. One then relies on the presence or absence of a precipitin band to determine the presence or absence, respectively, of a systemic candidiasis infection. The prior art embodiments of the agar gel diffusion technique left much to be desired. We have surprisingly found a way to harness the precipitin reaction into a convenient, reliable and rapid diagnostic procedure.

We have found that we are able to provide such a test if we incorporate into the agar layer a small amount of polyethylene glycol. This amount should preferably be about 1 to 2% by weight of the matrix material. The molecular weight should preferably be in the range of about 1,000 to 10,000. This incorporation not only accelerates any precipitin formation, but also significantly enhances the readability of the latter. Thus by the test system of our invention, the ordinary clinical laboratory technician can make a reliable determination within 24 hours and can detect about two-thirds of the positive reactions in about only 5 hours. It must be remembered that it is important to identify positives as soon as possible in order to begin the appropriate therapy.

In addition to *Candida albicans* which is clinically the most important infective species, the following uncommon but nevertheless systemically pathological species can also be detected by our test system: *C. krusei, C. parapsilosis, C. pseudotropicals* and *C. stellatoida. Torulopsis glabrata,* a clinically significant, non-candidal pathogenic fungus, can also be detected by our system.

The pH of the agar layer should be within the range of about 7 to 9.6, and preferably 8 to 9. An appropriate buffer is added in an amount sufficient to effect and maintain the foregoing pH. A preferred buffer is barbital, having a pH of 8.6 and an ionic strength of 0.025$\mu$. Examples of other useable buffers include N-tris-(hydroxymethyl) methylglycine (Tricine); cyclohexylamino-1-propane sulfonic acid (CAPS); N,N-bis-(2-hydroxyethyl) glycine (Bicine); N-2-hydroxyethylpiperazine-N' -2-ethane sulfonic acid (Hepes); N-tris-(hydroxymethyl) methyl-2-aminoethanesulfonic acid (TES); 1,4-Piperazine- bis-(ethanesulfonic acid) (Pipes); 3-(N-Morpholino) propanesulfonic acid (MOPS); tris-(hydroxymethyl) methyl-aminopropane sulfonic acid (TAPS): tricine-boric acid, tris-EDTA-boric acid and glycine-saline.

The soluble Candida antigens are prepared according to techniques known in the art. A suitable Candida strain, preferably the Tyson strain, is cultivated and the yeast-phase cells are ruptured. The soluble constituents are separated by differential centrifugation. A preferred means is mechanical rupture by violent agitation with glass beads in a suitable homogenizer such as the Braun MSK homogenizer or a Waring Blender. The crude soluble antigen solution is purified by sterile filtration and is preserved at low temperature storage. Such contemplated antigens comprise cytoplasmic protein antigens in addition to the polysaccharide antigen mannan found in the cell wall. The antigen solvent can simply be distilled water, preferably buffered, at a pH of 6 to 9 with a compatible buffer, e.g. phosphate-buffered saline (PBS), pH 7.2.

In a preferred embodiment of our invention we have found that it is desirable to include in the antigen solution an amount of mannan antigen in stoichiometric excess over that which would be reasonably anticipated in the sample of blood serum. The concentration of mannan antigen in the antigen solution should be in the range of 0.025–1 mg per ml and preferably 0.1–0.5 mg per ml. The concentration of protein antigens should be in the range of 0.5–10 mg per ml and preferably 1–6 mg per ml. In a preferred embodiment the weight ratio of protein antigens to mannan is in the range of 5–10 to 1. We have found that this embodiment lowers the amount of false positives which tend to all-too-commonly occur in the prior art candidiasis tests. Although we do not wish to limit our invention to the following possible theoretical explanation of this phenomenon, it appears to obviate visible precipitin formation occurring in the interaction between the antigen and low levels of antibodies which are commonly found in the blood sera of patients who do not evince a clinically significant systemic candidiasis infection. It seems that many individuals have at some time in their lives been exposed to Candida organisms and have formed antibodies in response thereto. Such antibodies remain in the blood long after threat of serious candidiasis is passed.

BRIEF DESCRIPTION OF THE DRAWING

FIG. 1 shows a top plan view of a test plate that may be used in the practice of the invention.

DETAILED DESCRIPTION OF THE INVENTION

In a highly preferred embodiment of this invention the test plate appears substantially as depicted in the FIGURE. That is, a shallow dish contains an agar layer covering substantially all of the bottom surface area of said dish, except for eight wells which define a square 15.4 by 15.4 mm, four wells of which each have a diameter of about 2.7 mm and constitute the corners of said square, and the remaining four wells each having a diameter of about 4 mm, the latter four wells also defining a square, said four larger wells being adapted to contain a blood serum sample from said host and said four smaller wells being adapted to contain an antigen solution.

The test method and system of our invention can be illustrated by reference to the FIGURE which is a preferred embodiment. A shallow plate or dish 1 contains an agar layer 3. A cover lid (not shown) should generally be seated over the dish (except during filling and reading periods), to protect aganinst atmospheric contamination. The dish may optionally be provided with projections 2 for ease in moving fthe dish and in removing its protective cover (not shown). The layer 3 is continuous, except for eight holes or wells 4–11 which are so arranged as to define a square of approximately 15.4 mm on each side. Four of the wells 8, 9, 10 and 11 are 2.7 mm in diameter and constitute the corners of this square. Larger wells 4, 5, 6 and 7 are 4 mm in diameter and themselves define a square of about 12.5 mm on each side. In other words, each larger well is colinear with and equidistant from its two closest smaller wells. Agar layer 3 contains 1 to 2% by weight (e.g. 1.5%) of a polyethylene glycol having a molecular weight of 1,000 to 10,000 (e.g. 6,000). The larger wells are filled by pipette with 20μ l of serum. Serum samples from four different patients can be placed in each of the respective larger wells or two or more wells can be used for duplicate runs on the same patient. Alternatively, one or more serum wells could be used as positive controls. Within 5 minutes of adding the serum to the larger wells the smaller wells should be filled with 10μ l of the antigen solution. The cover lid is replaced and the plates are incubated at ambient temperature for 24 hours.

The plates are read after 24 hours, although positive reactions can often be observed within 3 hours. The cover is removed and the agar layer is checked for precipitin lines, preferably using a dark-field light box. The area between the serum well and the antigen well is closely examined, preferably with a magnifying lens. If the agar is clear or there is just a halo of non-specific precipitate surrounding the serum well, the test is interpreted as negative for that serum sample. On the other hand, if there are one or more precipitin lines 12, 13, 14 between the serum and antigen wells, the test is interpreted as being positive for that serum sample. Rarely, a line may be seen with only one of the two antigen wells flanking the serum sample. In such event the test is still interpreted as positive.

The test plate of the FIGURE, together with a container housing the described antigen solution, comprises the convenient kit of this invention. The kit preferably comprises a second container housing a serum of known Candida content for purposes of providing a positive control serum. This provides a control to ensure that the laboratory technician is employing proper techniques.

Our test plate and kit can also be used to titer the extent of the Candida infection in those cases of positive reading. The patient's serum is diluted and dilutions of 1:2, 1:4, 1:8 and 1:16 are respectively placed in each of the four serum wells. The highest dilution showing a positive reaction in 48 hours is the titer for that serum. Such measurements are useful in monitoring the severity and progress of the infection.

Numerous variants of the diagnostic method, plate and kit described above will be apparent to one skilled in the art within the spirit of this invention.

What is claimed is:

1. In an in vitro test method for the diagnosis of systemic candidiasis in a mammalian host, said test method being based on precipitin formation between antibodies in a blood serum sample from said host and antigens in solution, said antibodies and antigens each diffusing through an agar layer maintained at a pH of 7 to 9.6, to encounter one another and form said precipitin, the improvement which comprises incorporating in said antigen solution a concentration of protein antigens in the range of 0.5 to 10 mg. per ml and a concentration of mannan antigen in the range of 0.025 to 1 mg. per ml, the weight ratio of said protein antigens to mannan being in the range of 5:1 to 10:1, said protein and mannan antigens prepared from the yeast phase, whereby false readings are reduced.

2. A method according to claim 1 wherein said agar layer contains about 1 to 2% by weight of a polyethylene glycol having an average molecular weight within the range of about 1,000 to 10,000.

3. A method according to claim 1 wherein said protein antigens are present in a concentration within the range of 1 to 6 mg. per ml and said mannan is present in a concentration within the range of 0.1 to 0.5 mg. per ml.

4. A method according to claim 3 wherein said agar layer contains about 1 to 2% by weight of a polyethylene glycol having an average molecular weight within the range of about 1,000 to 10,000.

5. An antigen solution for use in an in vitro test for systemic candidiasis comprising a concentration of protein antigens in the range of 0.5 to 10 mg. per ml and a concentration of mannan antigen in the range of 0.025 to 1 mg. per ml, the weight ratio of said protein antigens to mannan being in the range of 5:1 to 10:1 said protein and mannan antigens prepared from the yeast phase; said solution having a pH of 6 to 9.

6. An antigen solution according to claim 5 wherein said protein antigens are present in a concentration within the range of 1 to 6 mg. per ml and said mannan is present in a concentration of within the range of 0.1 to 0.5 mg. per ml.

* * * * *

UNITED STATES PATENT OFFICE
CERTIFICATE OF CORRECTION

Patent No. 4,051,232 Dated September 27, 1977

Inventor(s) Walter P. Protzman et al.

It is certified that error appears in the above-identified patent and that said Letters Patent are hereby corrected as shown below:

Column 1, line 16, "Should a reliable ddiagnosis" should read --- Should a reliable diagnosis ---. Column 3, line 36, "with projections 2 for ease in moving fthe dish" should read --- with projections 2 for ease in moving the dish ---.

Signed and Sealed this

*Fourteenth* Day of *March 1978*

[SEAL]

*Attest:*

RUTH C. MASON
*Attesting Officer*

LUTRELLE F. PARKER
*Acting Commissioner of Patents and Trademarks*